(12) United States Patent
Jacobs et al.

(10) Patent No.: US 6,610,047 B2
(45) Date of Patent: Aug. 26, 2003

(54) SINUS CANNULA

(75) Inventors: Joseph B. Jacobs, New York, NY (US); Dennis F. Creedon, Sandwich, MA (US)

(73) Assignee: E. Benson Hood Laboratories, Pembroke, MA (US)

( * ) Notice: Subject to any disclaimer, the term of this patent is extended or adjusted under 35 U.S.C. 154(b) by 0 days.

(21) Appl. No.: 09/947,874

(22) Filed: Sep. 6, 2001

(65) Prior Publication Data

US 2003/0045862 A1 Mar. 6, 2003

(51) Int. Cl.[7] .................................................. A61M 1/00
(52) U.S. Cl. ........................................... 604/540; 604/8
(58) Field of Search ................................. 604/540, 541, 604/94.01, 93.01, 164.11, 173, 164.1, 533–535, 246, 264, 539, 284

(56) References Cited

U.S. PATENT DOCUMENTS 3,835,863 A * 9/1974 Goldberg et al. ........... 604/284
4,469,483 A * 9/1984 Becker et al. ....... 128/DIG. 21

* cited by examiner

*Primary Examiner*—Weilun Lo
*Assistant Examiner*—Linh Truong
(74) *Attorney, Agent, or Firm*—Frommer Lawrence & Haug LLP; Ronald R. Santucci

(57) ABSTRACT

A cannula is described for insertion within the nose of a patient to provide drainage or to allow for postoperative suction of the sinus after surgery. The cannula is formed as an elongated tubular section with an anchoring end for insertion into the sinus. At the anchoring end of the cannula reinforced leaflets are provided as drainage channels and to serve as the anchoring aspect of the cannula.

10 Claims, 1 Drawing Sheet

SINUS CANNULA

BACKGROUND OF THE INVENTION

1. Field of the Invention

The present invention relates to a one-piece sinus cannula and more particularly to a cannula with a plurality of exterior drainage channels which allow drainage or suction to a central core of the cannula, the cannula sized to fit a nasal passage and sized to provide a normal sinus function to a patient after persistent frontal sinus surgery.

2. Brief Description of the Prior Art

In the practice of Functional Endoscopic Sinus Surgery (FESS), one of the factors in determining success is a continuing ability to maintain a drainage or a suctioning from the frontal sinus.

Available devices for drainage include cannula or catheter tubes which are inserted into the sinus wall during surgery. Existing catheters may be suitable for irrigation of the sinus but are limited in their drainage capabilities by such factors as a minimum number of drainage channels and the design of the drainage channels provided.

Existing catheters can also have anchorage problems in their ability to remain in a stable position in the sinus after insertion. When the catheters are inserted, the tubular shape of the end of the catheters permits rotating or horizontal movement in the sinus. This movement can lead to agitation and pain to the patient after surgery. This movement can also lead to the catheter being accidentally pulled out of the sinus. If the catheter is accidentally pulled out, problems such as pain to the patient and an interruption of post-operative suction or draining.

Thus, it is seen from the foregoing that there is a need for a device that avoids or minimizes the disadvantages associated with existing catheters used in sinus surgery.

SUMMARY OF THE INVENTION

An objective of the present invention is to provide a device which can maintain a reliable post-operative drainage of the sinus.

A further objective of the present invention is to provide a device which allows an easier and reliable post-operative suction of the sinus.

A still further objective of the present invention is to provide a device which can be manipulated for adequate placement in the sinus.

A still further objective of the present invention is to provide a device which is flexible during insertion into the sinus.

A still further objective of the present invention is to provide a device which adapts to the inconsistency of bone structure of individual patients.

A still further objective of the present invention is to provide a device which can be secured in the sinus.

A still further objective of the present invention is to provide a device which can be easily visualized with or without the assistance of x-ray equipment.

A still further objective of the present invention is to provide a device which can be trimmed or cut to size to suit the needs of individual patients.

To attain these objectives, there is provided a one-piece cannula which includes four drainage leaflets. Using four leaflets allows continued drainage if one or more of the leaflets becomes compromised by misplacement in the sinus or other factors. The leaflets are formed into channels which angle toward the hollowed center of the cannula and are surface-treated to be smooth. Both the angling and surface-treating features of the channel allow for more effective drainage of the sinus.

The underside of each leaflet forms a slope concluding with a thicker wall adjacent to the cannula. This thicker wall provides a more secure anchoring aspect to the cannula, with the result of preventing the cannula from being pulled out of the sinus. By using the anchoring aspect for a feedback, the physician can tug on the device in order to ensure correct and secure placement of the cannula. The sloping of the underside of each leaflet also allows flexibility during insertion and stable fixation during placement, eliminating the possibility of rotation or horizontal movement, while also being more forgiving to any inconsistency of bone structure within the sinus.

The cannula is preferably manufactured out of radiopaque silicone rubber. This is a soft material that has a white color, the white color providing ease of visualization with the naked eye or with the use of an x-ray. The length of the cannula allows for ease in suctioning and can be trimmed as needed.

BRIEF DESCRIPTION OF THE DRAWINGS

Thus by the present invention its objects and advantages will become readily apparent upon reading the following detailed description of the invention in conjunction with the accompanying drawing, in which.

DETAILED DESCRIPTION OF THE PREFERRED EMBODIMENTS

Figure 1:
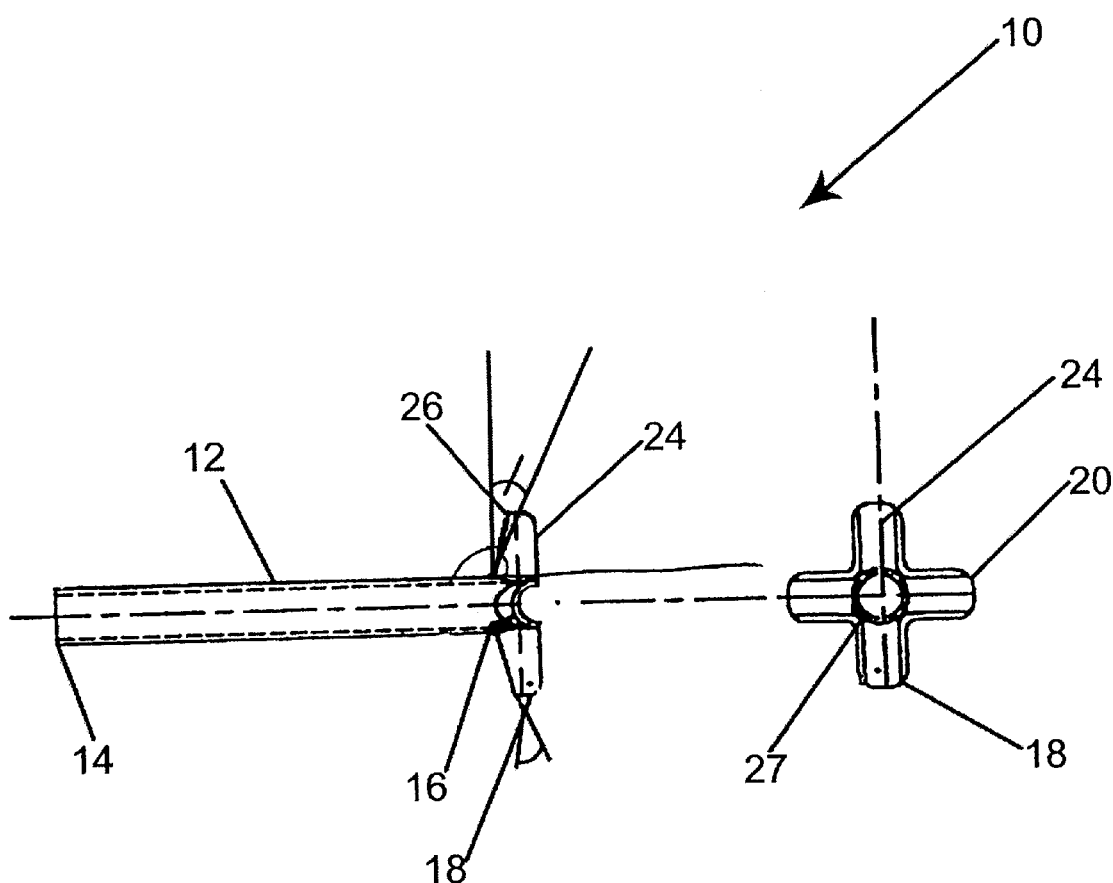
FIG. 1 depicts a side and end view of a sinus cannula of the present invention.

The present invention provides for a sinus cannula having a flexible tube and a plurality of leaflets positioned perpendicular to said flexible tube, each of said leaflets forming a channel from a collecting end to a connecting end 27, said connecting end 27 attached at an end of said flexible tube with said channel in fluid communication with said flexible tube, such that said channel provides a drainage path in a sinus from said collecting end to said flexible tube.

Referring now specifically to the drawing, wherein like reference numerals correspond to like elements throughout the represented views, one sees that FIG. 1 depicts a sinus cannula 10. The cannula 10 is a flexible tube 12 preferably manufactured out of medical grade radiopaque silicone rubber; however, other suitable materials may be used by those skilled in the art. The white color of the radiopaque silicone rubber allows visualization of the cannula with the naked eye or with an x-ray machine. Other features of the radiopaque silicone rubber are its flexibility, softness, and smoothness. These features allow the cannula to be used in a less invasive manner on the patient while enhancing the cannula's drainage capability of the sinus.

The overall length of the tube 12 is approximately forty-three millimeters with an inside diameter of approximately four millimeters and an outside diameter of approximately five millimeters. The length of tube 12 provides for ease in suctioning; however, tube 12 may be trimmed at proximal end 14. The length of tube 12 to be trimmed would depend on the individual needs of the patient.

At the distal end 16 of tube 12 are provided four surface-treated drainage leaflets 18. The leaflets extend perpendicular to the longitudinal axis of tube 12 and are spaced approximately ninety degrees from each other in a cross-like configuration. Each leaflet 18 has a collecting end 20 for capturing sinal fluid. Collecting end 20 is a thin parabolically shaped tip with a radius of approximately one-and-a-half millimeters. The distance from the collecting end of one leaflet to the collecting end of another leaflet is approximately sixteen millimeters. Formed in the collecting end 20 are channels 24. Each of the channels angle downward at approximately fifteen degrees to the distal end 16 of tube 12. The radius of each channel 24 is equal to the radius of the inside of tube 12. This equivalent radius allows proper drainage if the other drainage channels fail. The form and angular descent of the channels 24 along with the surface treatment of the channels allows effective drainage to the hollow core of tube 12.

The underside 26 of channel 24 thickens as it approaches distal end 16, thereby presenting a thicker wall adjacent to the tube 12 of the cannula 10. This thicker wall provides an anchoring aspect to the cannula 10 preventing the possibility of pulling the cannula through the sinus. Additionally, the anchoring aspect provides a feedback to the physician during placement, ensuring flexibility during insertion and stable fixation of the cannula 12. The anchoring aspect also eliminates or reduces the possibility of rotation or horizontal movement of the cannula within the sinus.

The foregoing description of the preferred embodiment of the invention has been presented for purposes of illustration and description. It is not intended to be exhaustive or to limit the invention to the precise form disclosed, and obviously many modifications and variations are possible in light of the above teaching. For example, the number and arrangement of drainage channels may be modified to suit various types of patients (ie: infants). Such modifications and variations that may be apparent to a person skilled in the art are intended to be included within the scope of this invention as defined by the accompanying claims.

We claim:

1. A sinus cannula, comprising:
   a flexible tube comprising a radiopaque material; and
   a plurality of leaflets positioned perpendicular to said flexible tube, each of said leaflets forming a channel from a collecting end to a connecting end, said connecting end attached at an end of said flexible tube with said channel in fluid communication with said flexible tube, such that said channel provides a drainage path in a sinus from said collecting end to said flexible tube, wherein the channel of the leaflet angles away from the flexible tube at an angle to allow for drainage, and wherein a thickness of the channel increases from said collecting end to said connecting end such that said connecting end provides an anchoring area within a sinus.

2. The sinus cannula of claim 1, wherein said leaflets are surface treated such that a flow in said channels is enhanced.

3. The sinus cannula of claim 1, wherein the channel of the leaflet angles away from the flexible tube.

4. The sinus cannula of claim 1, wherein the channel of the leaflet angles away from the flexible tube relative to the longitudinal axis of the flexible tube.

5. The sinus cannula of claim 4, wherein the angle is approximately 15 degrees.

6. The sinus cannula of claim 4, wherein a thickness of the channel increases from said collecting end to said connecting end such that said connecting end provides an anchoring area within a sinus.

7. The sinus cannula of claim 1, wherein said cannula is manufactured from medical grade radiopaque silicone rubber.

8. The sinus cannula of claim 1, wherein an overall length of said cannula is approximately forty-three millimeters thereby providing the sinus cannula with a trimmable length.

9. The sinus cannula of claim 1, wherein an outside diameter of said flexible tube is approximately five millimeters.

10. A sinus cannula, comprising:
    a flexible tube comprising a medical grade radiopaque silicone rubber; and
    a plurality of leaflets positioned perpendicular to said flexible tube, each of said leaflets forming a channel from a collecting end to a connecting end, said connecting end attached at an end of said flexible tube with said channel in fluid communication with said flexible tube, such that said channel provides a drainage path in a sinus from said collecting end to said flexible tube, wherein the channel of the leaflet angles away from the flexible tube at an angle to allow for drainage, and wherein a thickness of the channel increases from said connecting end to said connecting end such that said connecting end provides an anchoring area within a sinus.

* * * * *